United States Patent
Vezinet et al.

(10) Patent No.: US 9,714,407 B2
(45) Date of Patent: Jul. 25, 2017

(54) DEVICE FOR APPLYING AN ELECTROMAGNETIC FIELD TO A BIOLOGICAL SAMPLE

(71) Applicant: COMMISSARIAT A L'ENERGIE ATOMIQUE ET AUX ENERGIES ALTERNATIVES, Paris (FR)

(72) Inventors: Rene Vezinet, Bio (FR); Mathieu Croizer, Brive (FR); Jean-Christophe Diot, Gramat (FR); Alexandre Catrain, Le Vigan (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 149 days.

(21) Appl. No.: 14/648,977

(22) PCT Filed: Dec. 2, 2013

(86) PCT No.: PCT/EP2013/075272
§ 371 (c)(1),
(2) Date: Jun. 2, 2015

(87) PCT Pub. No.: WO2014/086725
PCT Pub. Date: Jun. 12, 2014

(65) Prior Publication Data
US 2015/0299640 A1     Oct. 22, 2015

(30) Foreign Application Priority Data

Dec. 4, 2012 (FR) ..................... 12 61622

(51) Int. Cl.
C12M 1/42       (2006.01)
C12M 1/22       (2006.01)
C12N 13/00      (2006.01)

(52) U.S. Cl.
CPC ............ C12M 35/02 (2013.01); C12M 23/10 (2013.01); C12N 13/00 (2013.01)

(58) Field of Classification Search
CPC ........ C12N 13/00; C12M 35/02; C12M 23/10
See application file for complete search history.

(56) References Cited

U.S. PATENT DOCUMENTS 5,536,267 A * 7/1996 Edwards et al. ........ C22F 1/183
                                                        604/22
6,326,177 B1 * 12/2001 Schoenbach
                                 et al. .................. A61B 18/1206
                                                        435/173.7

(Continued)

OTHER PUBLICATIONS

J. Thomas Camp, et al., "Bioelectric Studies with Subnanosecond Pulsed Electric Fields," PPC '09, IEEE, XP031615053, Jun. 28, 2009, pp. 876-879.

(Continued)

*Primary Examiner* — Gautam Prakash
(74) *Attorney, Agent, or Firm* — Oblon, McClelland, Maier & Neustadt, L.L.P.

(57) ABSTRACT

A device for applying an electromagnetic field to a biological feedstock sample is disclosed. The device includes a coaxial electrical structure including a center conductor and a ground conductor which surrounds the center conductor, a load including a resistor and the biological feedstock sample being positioned between one end of the center conductor and a conductive wall which extends the ground conductor into a plane substantially perpendicular to the axis of the center conductor, the resistor having a first end connected to the center conductor and a second end connected to the conductive wall, the resistor defining an internal volume wherein the biological feedstock sample is placed.

10 Claims, 6 Drawing Sheets

(56) References Cited

U.S. PATENT DOCUMENTS

2002/0010491 A1\* 1/2002 Schoenbach et al. .......... A61B 18/1206 607/2
2011/0137229 A1\* 6/2011 Palti et al. ............ A61N 1/40 604/20

OTHER PUBLICATIONS

Tammo Heeren, et al., "250 kV Sub-nanosecond Pulse Generator with Adjustable Pulse-width," IEEE Transactions on Dielectrics and Electrical Insulation, vol. 14, No. 4, XP011381654, Aug. 2007, pp. 884-888.
Karl H. Schoenbach, et al., "The Effect of Intense Subnanosecond Electrical Pulses on Biologicals Cells," IEEE Transactions on Plasma Science, vol. 36, No. 2, XP011206838, Apr. 2008, pp. 414-422.
Aude Silve, et al., "Nanosecond-Duration Electric Pulse Delivery In Vitro and In Vivo: Experimental Considerations," IEEE Transactions on Instrumentation and Measurement, vol. 61, No. 7, XP011445957, Jul. 2012, pp. 1945-1954.
International Search Report issued Jan. 7, 2014 in PCT/EP2013/075272 filed Dec. 2, 2013.

\* cited by examiner

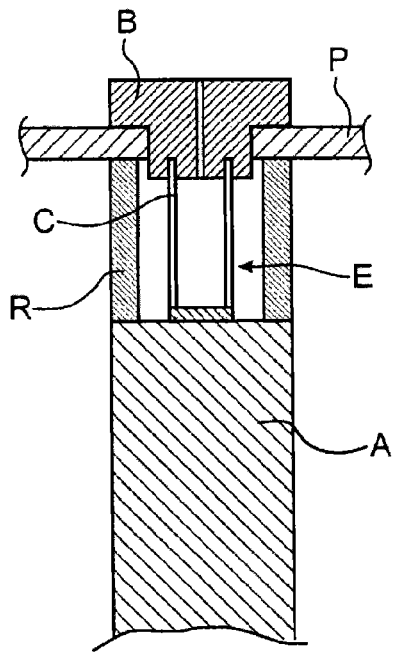 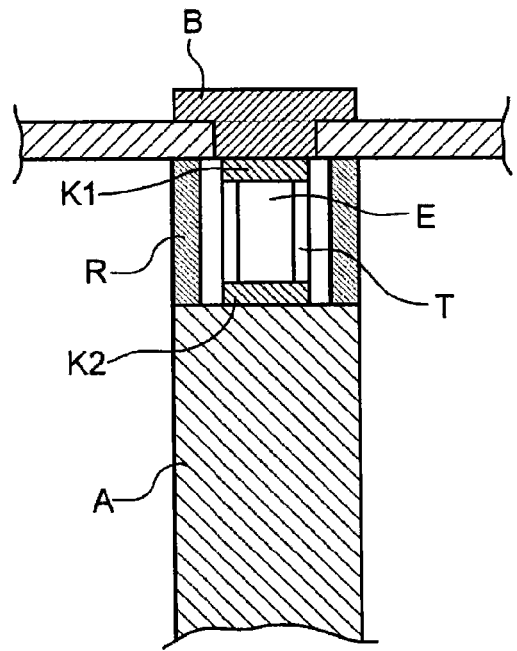
FIG.6A  FIG.6B
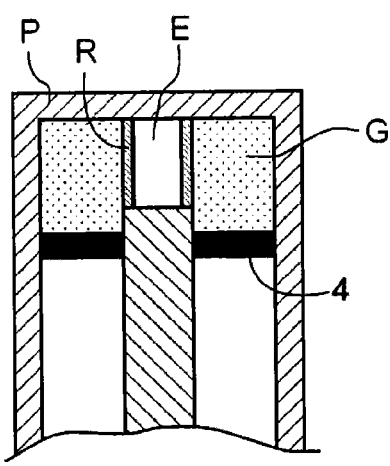 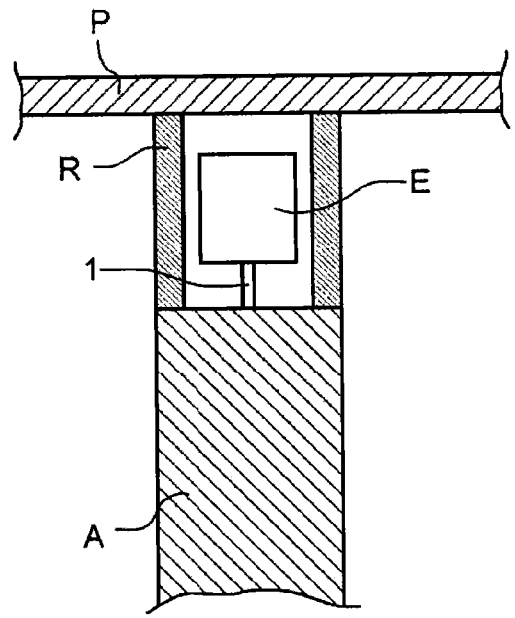
FIG.6C  FIG.6D

DEVICE FOR APPLYING AN ELECTROMAGNETIC FIELD TO A BIOLOGICAL SAMPLE

TECHNICAL FIELD AND PRIOR ART

The invention relates to a device for applying an electromagnetic field to a biological sample.

The field of the invention is that of bio-electromagnetism the aim of which is to study the effects of electromagnetic fields on living organisms.

Studies conducted within the scope of bio-electromagnetism require experimental systems able to expose various biological organisms, of various sizes and natures, to electromagnetic fields.

The amplitudes of electromagnetic fields can be high (several tens kV/cm) and the spectral content of the signals ranges from the continuous spectrum to very high frequencies (beyond one GHz).

To date, a great variety of techniques exist for the application of electromagnetic fields as, for example:
"plane waves" type exposure systems;
reverberation chambers;
wave guides;
wire patch cell;
radial transmission line;
Crawford cells and TEM (Transverse ElectroMagnetic) cells;
the coaxial load resistor device disclosed in document "BIOELECTRICAL STUDIES WITH SUBNANO-SECOND PULSED ELECTRIC FIELDS" (J. Thomas Camp, Shu Xiao, Stephen J. Beebe, Peter F. Blackmore, and Karl H. Schoenbach; Frank Reidy Research Center for Bioelectrics, Old Dominion University, Norfolk, Va.).

The main characteristics and drawbacks of the techniques of prior art will be set forth below.

The "plane waves" type exposure systems use radiating antennas which have to be placed in anechoic chambers, which are expensive facilities hardly implantable in a biology laboratory. This is a real drawback.

Reverberation chambers exclusively operate in a sinusoidal mode. Therefore, it is not possible to use pulses, which is a drawback. Besides, their installation is often very awkward and results in a bulky structure.

Wave guides also exclusively operate in a sinusoidal mode (no pulse) and their dimensions depend on the frequencies used.

The wire patch cell uses a single pole wire patch antenna and exclusively operates in a sinusoidal mode (no pulse) on a low bandwidth.

The radial transmission line uses a center cone antenna which generates a transverse electromagnetic wave. The passband of this device is also restricted.

Crawford cells (closed cells) and TEM cells (open cells) are rectangular shaped transmission lines. These cells are capable of generating electric and magnetic fields which are uniform and perpendicular to each other (TEM mode) in the test zone. They are able to propagate a DC current and, hence, are well suitable for the use of single pole or dual pole transient signals. Their use is however restricted in terms of permissible maximum voltage and passband/useful dimensions trade-off. The coaxial/biplate or coaxial/triplate geometrical transition is complex to make for high frequencies, particularly with high voltages. Besides, the presence of the object under test is de facto an obstacle which causes distortion in the electromagnetic field in the test zone.

The coaxial load resistor device disclosed in document "BIOELECTRICAL STUDIES WITH SUBNANOSECOND PULSED ELECTRIC FIELDS" is suggested for in vitro applications wherein subnanosecond pulses are applied to aqueous suspensions. This assembling is represented in FIG. 1. It consists of a coaxial line L closed at its end by a load Ch.

The coaxial line L conveys the electromagnetic wave to the load Ch. The line L comprises a center conductor A and a ground peripheral conductor M1. The impedance of the load Ch matches the impedance of the coaxial line L such that the incident wave which reaches the load is not reflected. The load Ch comprises a center conductor K which extends the center conductor A of the line L and a ground peripheral conductor M2 which extends the ground peripheral conductor M1. The ground peripheral conductor M2 is closed by a wall P formed in a plane with a straight cross section perpendicular to the axis of the coaxial line. A resistor R has a first terminal electrically connected to the end of the center conductor K and a second terminal electrically connected to the wall P of the ground peripheral conductor M2. Whereas the center conductor A has a constant diameter all along the line L, the diameter of the center conductor K widens and then narrows between the center conductor A and the first terminal of the resistor R. Likewise, whereas the distance which separates the ground peripheral conductor M1 from the center conductor A remains constant all along the line L, the distance which separates the ground peripheral conductor M2 from the conductor K strongly widens and then narrows to the wall P which closes the load Ch. The resistor R is lined up with the center conductors A and K. The sample E to be tested is placed between the end of the coaxial conductor K and the wall P and surrounds the resistor R.

Such an assembling is complex to be machined because of the dimension variations it imposes. Besides, since the sample E surrounds the resistor R, it is necessary to provide samples the center part of which is hollowed out. This also represents another drawback, because it imposes real constraints regarding the geometry of the samples.

The invention does not have these drawbacks.

DISCLOSURE OF THE INVENTION

Indeed, the invention relates to a device for applying an electromagnetic field to a biological feedstock sample, the device comprising a coaxial electrical structure having a center conductor and a ground conductor which surrounds the center conductor, a load consisting of an electrical resistor and the biological feedstock sample being positioned between one end of the center conductor and a conductive wall which extends the ground conductor into a plane substantially perpendicular to the axis of the center conductor, the electrical resistor having a first end connected to the center conductor and a second end connected to the conductive wall. The electrical resistor defines an internal volume wherein the biological feedstock sample is placed.

According to a first embodiment of the invention, the resistor consists of an assembly of parallel solid resistive tubes which define the internal volume wherein the biological feedstock sample is placed.

According to a second embodiment of the invention, the resistor R consists of a hollow cylinder which defines the internal volume wherein the biological feedstock sample is placed.

BRIEF DESCRIPTION OF THE FIGURES

Further characteristics and advantages of the invention will appear upon reading the description that follows, made in reference to the appended figures, among which:

FIGS. 6A-6D represent different variants of the device of the invention;

Throughout the figures, same references designate same elements.

DETAILED DISCLOSURE OF EMBODIMENTS OF THE INVENTION

Figure 2:
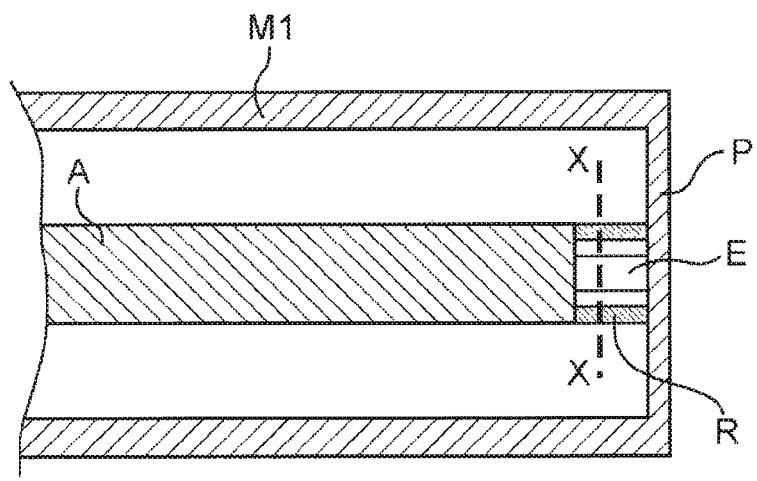
FIG. 2 represents a device able to apply an electromagnetic field to a biological sample according to the invention.

FIG. 2 represents a device able to apply an electromagnetic field to a biological sample according to the invention.

The device comprises a coaxial cable closed by a load. The coaxial cable consists of a center conductor A with a constant diameter and a ground peripheral conductor M1 the distance of a center conductor of which remains constant to the end of the center conductor. The load is positioned at the end of the center conductor. It consists of a hollow cylindrical tube shaped resistor R and a biological feedstock sample E positioned within the hollow cylindrical tube formed by the resistor. The hollow cylindrical tube has preferentially an external diameter identical to the diameter of the center conductor A and extends the latter to a planar conductive wall P formed in a plane with a straight cross section perpendicular to the axis of the coaxial cable and which closes the ground peripheral conductor M1. The biological feedstock sample E has a first face in contact with the end of the center conductor and a second face, opposite the first face, in contact with the wall P. The biological feedstock sample E is a solid or liquid. In the case where the sample is solid, it may be placed as such within the tube formed by the resistor R. In the case where the sample is liquid, it is placed in a hollow cylindrical tube made of an electrically insulating material. In any case, the solid or liquid biological feedstock is in contact with the end of the center conductor A and the conductive wall P.

Figure 3A:
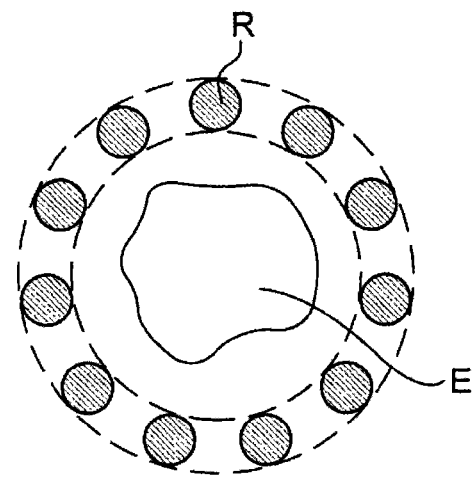
FIGS. 3A and 3B represent two variants of a transverse cross section view of a device of the invention.
Figure 3B:
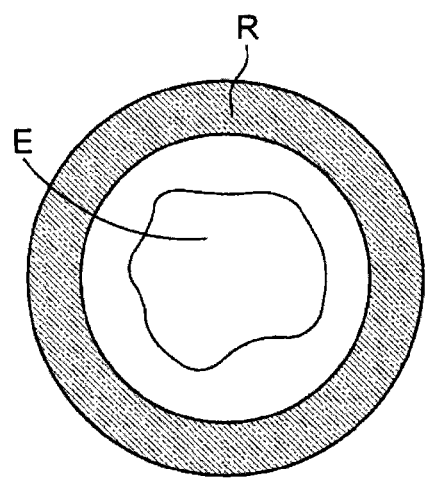

FIGS. 3A and 3B represent two variants of a transverse cross section view along the axis XX of a device of the invention.

As illustrated in FIGS. 3A and 3B, the resistor R consists, for example, of an assembly of parallel solid resistive cylindrical tubes (FIG. 3A) or a single hollow cylindrical resistive tube (cf. FIG. 3B) wherein the biological sample is accommodated. Advantageously, the biological feedstock sample E does not have a center recess. In the geometrical configuration of the device of the invention, the electric field which is present in the space surrounded by the resistor is governed by the voltage at the terminals of the resistor. As a result, the amplitude of this field has a great homogeneity. Advantageously, the sample is placed in this zone in accordance with the invention. The entire volume of the sample is thus subjected to an electric field having an amplitude of a great homogeneity.

Figure 4A:
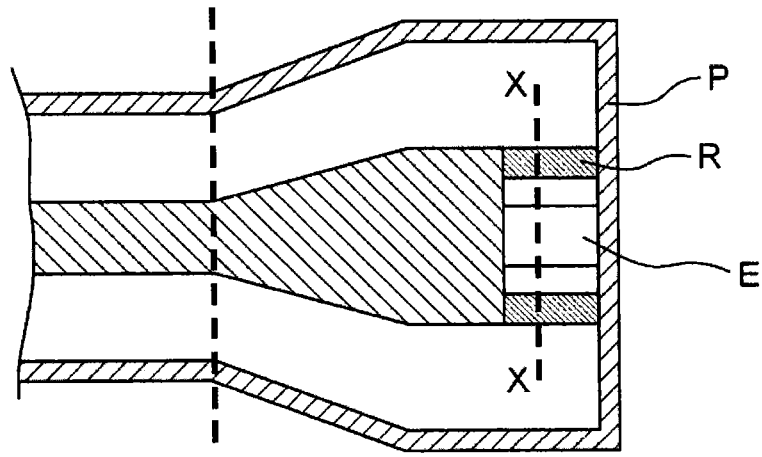
FIGS. 4A and 4B represent modifications of the device represented in FIG. 2.
Figure 4B:
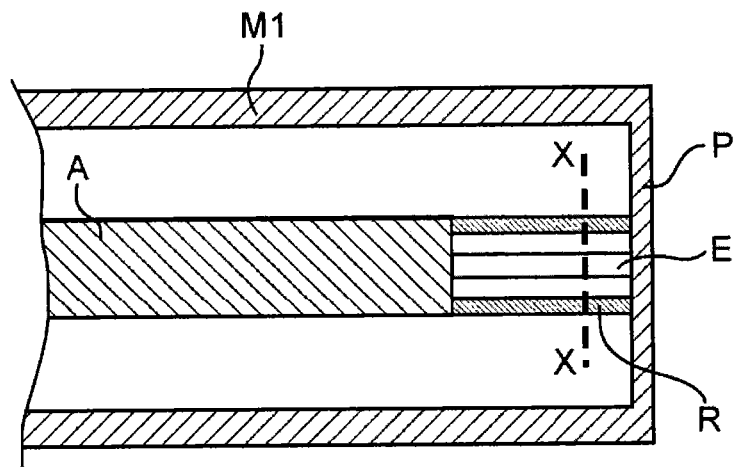

FIGS. 4A and 4B represent modifications of the device represented in FIG. 2.

FIG. 4A illustrates the case where the coaxial cable widens at its end such that the assembling of bulkier samples is allowed. Assembling the sample is besides identical to the assembling of the first embodiment of the invention. A load resistor surrounds the sample, the load resistor being formed by a plurality of an assembly of parallel solid resistive tubes (FIG. 3A) or a single hollow cylindrical resistive tube (FIG. 3B). The load resistor electrically connects the center conductor of the coaxial cable to a planar conductive wall P which extends the ground conductor and which resistor is formed in a plane with a straight cross section perpendicular to the axis of the coaxial cable. The load resistor thus locally governs the direction of the electric field which is consequently axial in the entire volume internal to the resistive load. Advantageously, the sample is placed in this internal volume in accordance with the invention.

FIG. 4B illustrates the case where the sample E is substantially longer than in the case of FIG. 2, all other things being equal. In this case, for the purposes of impedance matching, the ground conductor M1 moves closer to the resistor R before reaching the wall P.

Figure 5:
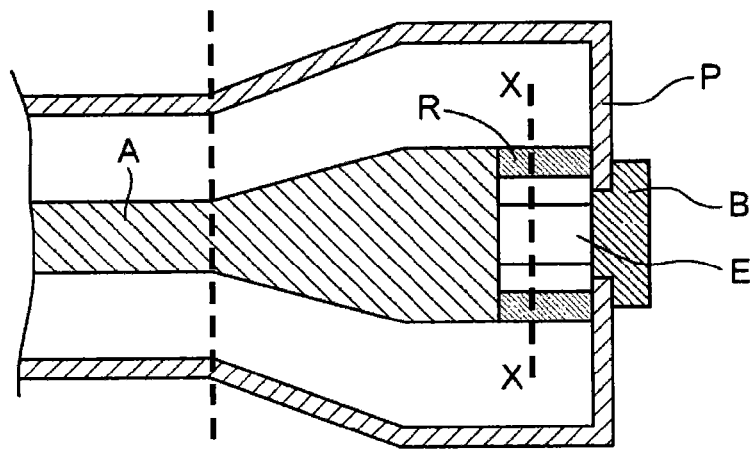
FIG. 5 represents a first improvement of the device of the invention.

FIG. 5 represents a first improvement in the device of the invention. According to this improvement, a removable plug or trapdoor B is placed at the end of the device in order to gain access to the sensitive volume of the sample. The wall P is then pierced with an aperture which is closed by the plug or trapdoor. The plug or trapdoor is an electrically conductive part, for example of metal. The plug can be solid or drilled. In the latter case, filling or purge ports, for example, pass therethrough.

FIGS. 6A-6D represent different alternatives of the device of the invention.

FIG. 6A corresponds to a case where the plug B is attached to the sample E. The biological feedstock, being solid or liquid, is then placed in a bowl C which is inserted in the plug B. The bowl C has a side wall made of an electrically insulating material and a bottom made of an electrically conductive material which is in contact with the end of the center conductor. The biological feedstock present in the bowl C is in contact with the plug and with the bottom of the bowl. It is then advantageously possible to change very simply the sample by removing the plug and by placing a new plug or the same plug equipped with another sample. The contact between the end of the center conductor and the bottom of the bowl C is preferably a flexible contact.

FIG. 6B represents the case where the biological feedstock is contained in a removable shell consisting of a hollow cylindrical tube T made of an electrically insulating material closed by two flat electrically conductive elements K1, K2. The flat electrically conductive elements K1, K2 are in respective contact with an electrically conductive plug B and with the end of the center conductor A. The electrically conductor plug B is placed in the wall P. It is then advantageously possible to change the sample by removing the plug B.

FIG. 6C represents the case where, to improve the voltage performances, a liquid (for example Perfluoropolyether oil) or gas G (for example gas SF6) insulator submerges the resistor R and the biological feedstock sample. An electrically insulating wall 4 substantially parallel to the conductive wall P is then placed between the center conductor A and the ground conductor M1 to define the volume contained by the resistor R, the sample E and the gas or liquid. This embodiment of the invention is compatible with the presence of a plug in the wall P (not represented in FIG. 6C).

FIG. 6D represents the case where the biological feedstock sample is a solid or complex object OS (for example Petri dish, animal, etc.) which is electrically insulated from the center conductor A and the conductive wall P. The sample E is then placed on a stand 1 made of an electrically insulating material. This embodiment of the invention is also compatible with the presence of a plug B in the wall P (not represented in the figure).

In all the cases mentioned above, a high voltage use, for example a 25 kV voltage, results in a particular choice of the electrically insulating materials used and the resistive material which makes up the resistor R, as well as a particular choice of geometries (for example avoidance of triple point geometries). By way of non limiting example, the electrically insulating material used for the previously mentioned tubes C and T can be, for example, polypropylene, and the resistive material of the resistor R can be, for example, a carbon filled ceramics.

Figure 7:
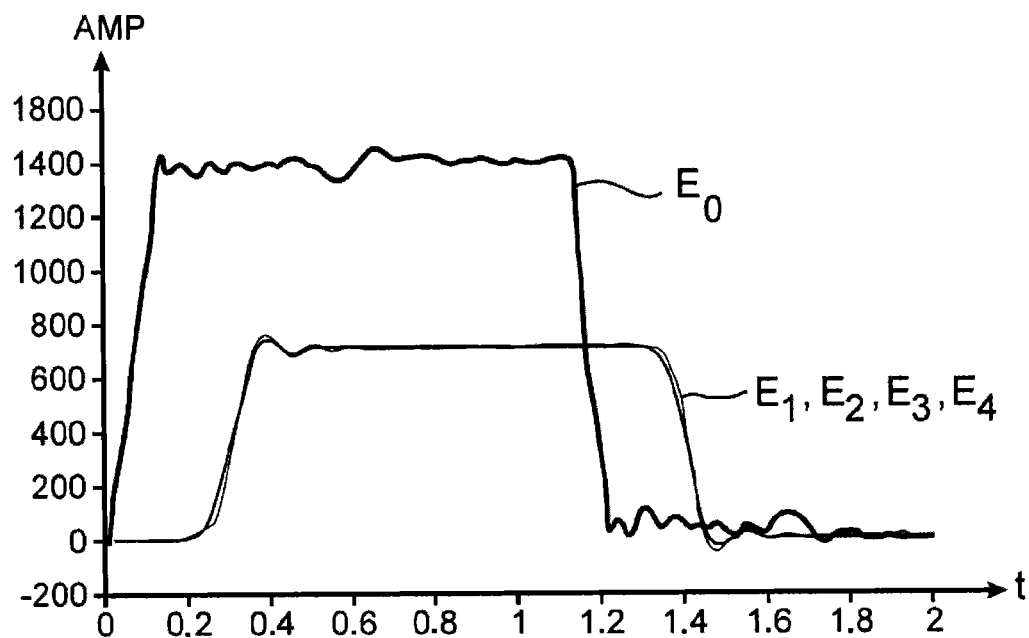
FIGS. 7 and 8 illustrate simulation results of the variation as a function of time in the amplitude of the electric field which is obtained using a device of the invention, respectively in the case of an empty sample and in the case of a sample filled with water.
Figure 8:
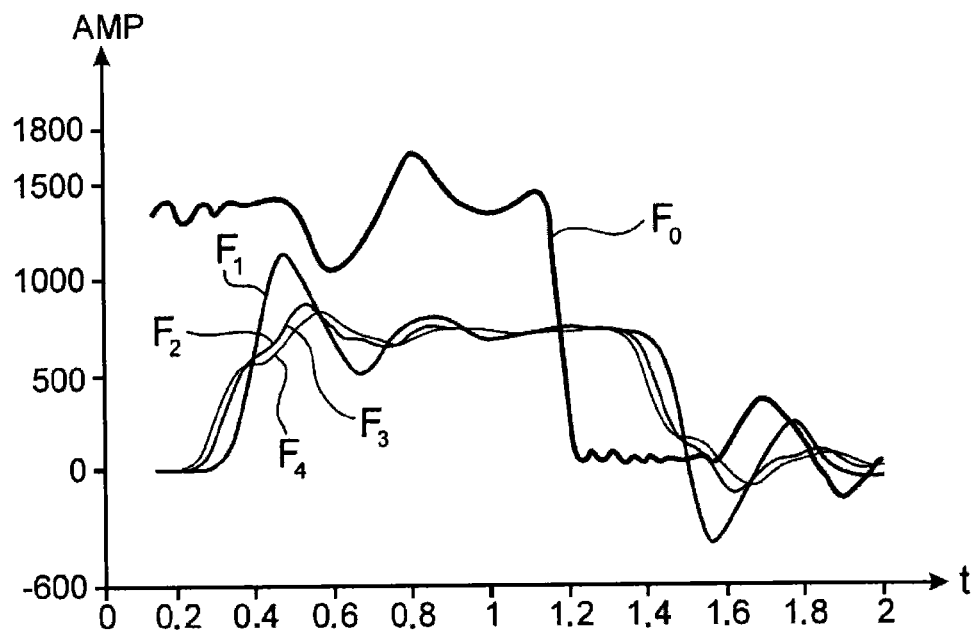
Figure 9:
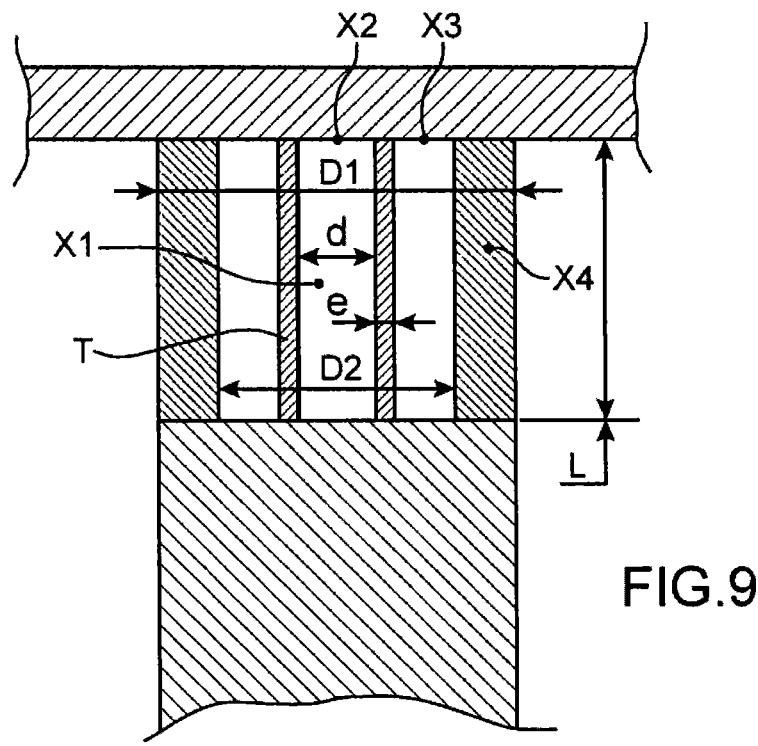
FIG. 9 illustrates a location of points of the device of the invention where the simulation of FIGS. 7 and 8 is performed.

FIG. 7 illustrates simulation results of the variation as a function of time in the amplitude AMP of the electric field which is obtained, in an empty mode, using a device in accordance with that of FIG. 2 and a detailed view of which is given in reference to FIG. 9. FIG. 8 illustrates the results obtained, for the same structure, with a water sample. The amplitude AMP is expressed in V/m and the time t is expressed in nanoseconds.

The resistor R is a 50Ω resistor made by a solid hollow cylinder with a length L equal to 10 mm, an external diameter D1 equal to 20 mm and an internal diameter D2 equal to 14 mm. The hollow cylindrical tube T likely to contain the biological liquid has an internal diameter d of 4 mm and a thickness e of 1 mm. The biological liquid column likely to be subjected to an electromagnetic field thus has a diameter of 4 mm and a length of 10 mm. The coaxial cable having a characteristic impedance equal to 50Ω is excited by a trapezoidal pulse with a duration of 1 ns, a rise time of 100 ps and amplitude of 7 V. In FIG. 7, the curve $E_0$ represents the amplitude of the electric field at the input of the coaxial cable (input pulse) and the curves $E_1$, $E_2$, $E_3$ and $E_4$ represent, respectively:

the amplitude of the electric field at a point X1 located in the volume intended to contain the biological feedstock (cf. FIG. 9),
the amplitude of the electric field at a point X2 located on the face of the wall P likely to be in contact with the biological feedstock,
the amplitude of the electric field at a point X3 located outside the inner space defined by the resistor R, on the face of the wall P located opposite the center conductor,
the amplitude of the electric field at a point X4 located inside the resistor R.

It can be observed that, in an empty mode, the curves $E_1$, $E_2$, $E_3$ and $E_4$ are advantageously the same.

In FIG. 8, the curve $F_0$ represents the amplitude of the electric field at the input of the coaxial cable (input pulse) and the curves $F_1$, $F_2$, $F_3$ and $F_4$ represent, respectively:

the amplitude of the electric field at the point X1,
the amplitude of the electric field at the point X2,
the amplitude of the electric field at the point X3,
the amplitude of the electric field at the point X4.

The curves F2 and F3 are advantageously the same and, if the other curves are not perfectly superimposed, it clearly appears that the homogeneity of the amplitude of the electric field remains excellent.

Figure 10:
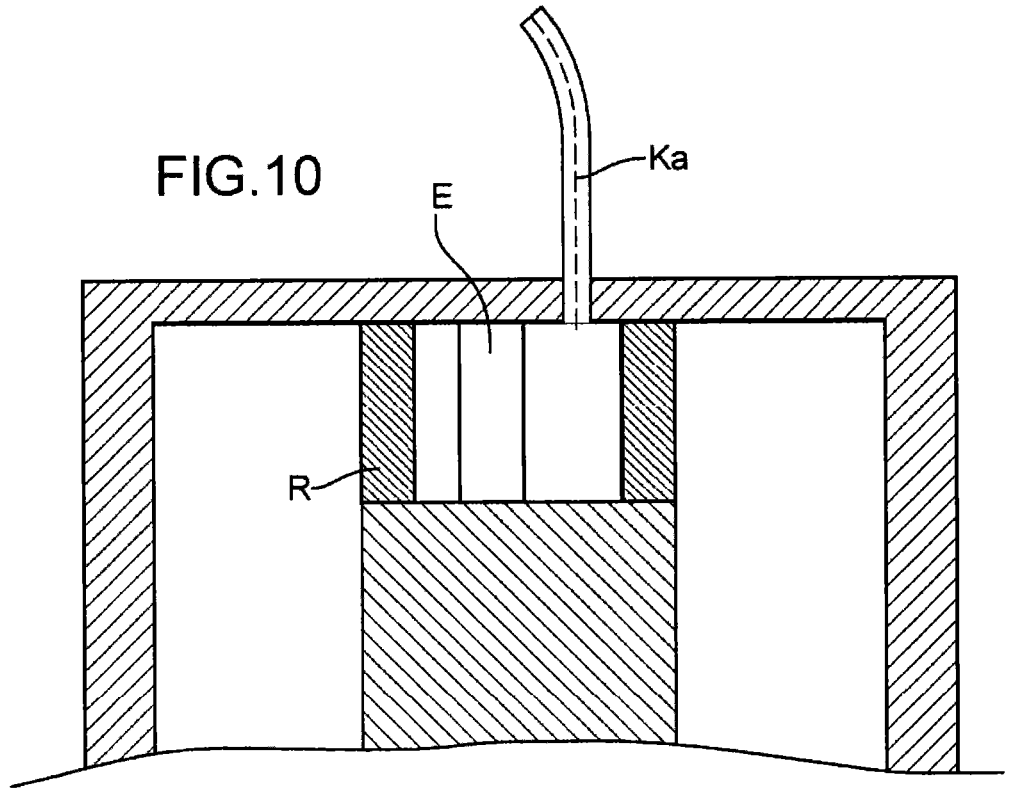
FIG. 10 illustrates a second improvement in the device of the invention.

FIG. 10 illustrates a second improvement in the device of the invention.

Figure 1:
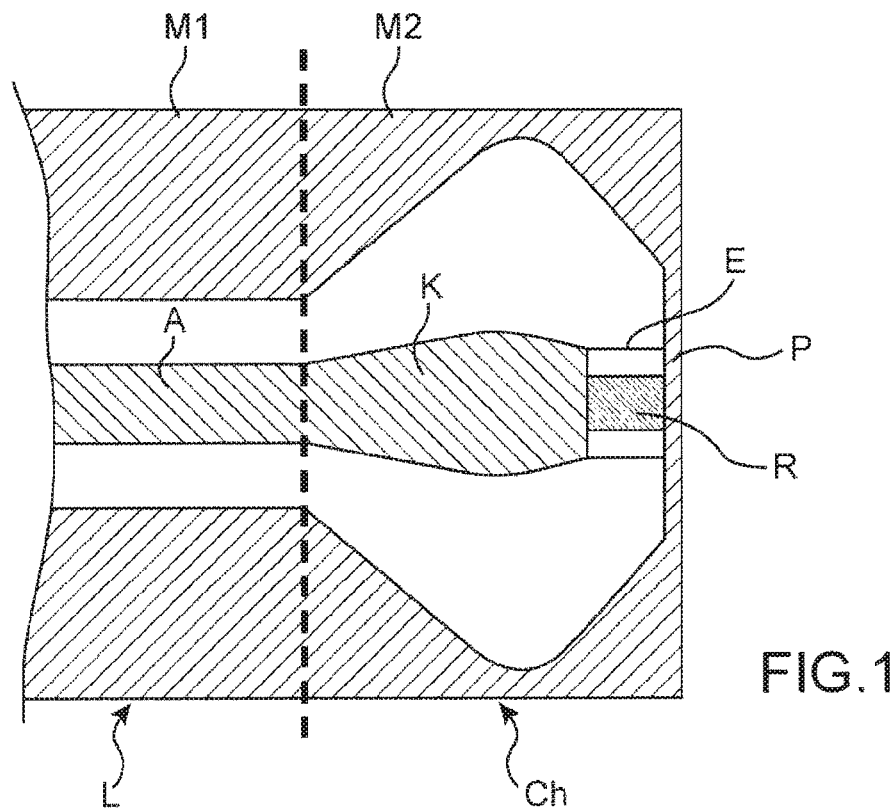
FIG. 1, already described, represents a coaxial load resistor device disclosed in document "BIOELECTRICAL STUDIES WITH SUBNANOSECOND PULSED ELECTRIC FIELDS"

According to this second improvement, an antenna is placed in the wall P to take amplitude values of the electric field at the previously defined point X3. This antenna is made, for example, using a coaxial cable Ka. Indeed, in reference to FIG. 8, it is possible to observe that the amplitude measurement of the electric field at the point X3 is perfectly representative of an electric field measurement at the point X2 and nearly representative of an electric field measurement at the point X1. Thus, it is possible, during a manipulation, to monitor the amplitude of the electric field which is applied to the biological sample based on a measurement made at the point X3. Such a monitoring is not possible with the devices of prior art and, in particular, with the device described in FIG. 1 which has a very strong amplitude scattering of the field at the sample, hence a measurement carried out at a first point cannot be representative of a measurement carried out at a point adjoining the first point.

The invention claimed is:

1. A device for applying an electromagnetic field to a biological feedstock sample, the device comprising:
   a coaxial electrical structure including a center conductor and aground conductor which surrounds the center conductor;
   a load including an electrical resistor; and
   the biological feedstock sample being positioned between one end of the center conductor and a conductive wall which extends the ground conductor into a plane substantially perpendicular to the axis of the center conductor,
   the electrical resistor having a first end connected to the center conductor and a second end connected to the conductive wall,
   the electrical resistor defining an internal volume wherein the biological feedstock sample is placed.

2. The device according to claim 1, wherein the electrical resistor includes an assembly of parallel solid resistive tubes which define an internal volume wherein the biological feedstock sample is placed.

3. The device according to claim 1, wherein the electrical resistor includes a hollow cylinder which defines an internal volume wherein the biological feedstock sample is placed.

4. The device according to claim 1, further comprising a removable plug or trapdoor placed in the electrically conductive wall to allow access to the biological feedstock sample.

5. The device according to claim 4, wherein the biological feedstock is contained in a bowl which is inserted in the plug or trapdoor, the bowl having a side wall made of an electrically insulating material and a bottom made of an electrically conductive material in contact with the end of the center conductor.

6. The device according to claim 4, wherein the biological feedstock is contained in a shell including a hollow cylindrical tube made of an electrically insulating material closed by two electrically conductive planar elements in respective contact with the plug or trapdoor and with the end of the center conductor.

7. The device according to claim 1, wherein the biological feedstock is contained in an enclosure including a surface fraction of the conductive wall, by a surface fraction of the end of the center conductor located facing the surface fraction of the conductive wall and by a hollow cylindrical tube made of an electrically insulating material located between the conductive wall and the end of the center conductor.

8. The device according to claim 1, wherein the biological feedstock is a solid body.

9. The device according to claim 8, wherein the solid body is a Petri dish, an object, or an animal.

10. The device according to claim 1, wherein an electrically insulating wall placed between the center conductor and the ground conductor defines a closed volume which contains the resistor and the biological feedstock sample, an electrically insulating liquid or gas soaking a head space of the closed volume.

\* \* \* \* \*